US008283352B2

(12) United States Patent
Otoda et al.

(10) Patent No.: US 8,283,352 B2
(45) Date of Patent: Oct. 9, 2012

(54) SOLUBILIZATION PREPARATION

(75) Inventors: Kazuya Otoda, Ibaraki (JP); Mayumi Nakamura, Ibaraki (JP); Teruko Ariyama, Ibaraki (JP); Takashi Nakagawa, Ibaraki (JP)

(73) Assignee: Dainippon Sumitomo Pharma Co., Ltd., Osaka-shi, Osaka (JP)

( * ) Notice: Subject to any disclaimer, the term of this patent is extended or adjusted under 35 U.S.C. 154(b) by 273 days.

(21) Appl. No.: 11/922,015

(22) PCT Filed: Jun. 12, 2006

(86) PCT No.: PCT/JP2006/311739
§ 371 (c)(1),
(2), (4) Date: Dec. 12, 2007

(87) PCT Pub. No.: WO2006/134864
PCT Pub. Date: Dec. 21, 2006

(65) Prior Publication Data
US 2009/0286805 A1    Nov. 19, 2009

(30) Foreign Application Priority Data
Jun. 13, 2005  (JP) ................... 2005-172725

(51) Int. Cl.
*A61K 31/497*  (2006.01)
(52) U.S. Cl. .................................. 514/254.02
(58) Field of Classification Search ............... 514/254.02
See application file for complete search history.

(56) References Cited

U.S. PATENT DOCUMENTS

| 5,532,372 | A | 7/1996 | Saji et al. | |
| 6,458,373 | B1 * | 10/2002 | Lambert et al. | 424/405 |
| 6,616,941 | B1 | 9/2003 | Seo et al. | |
| 2003/0158158 | A1 * | 8/2003 | Fujimoto | 514/167 |
| 2004/0028741 | A1 | 2/2004 | Fujihara | |
| 2006/0142276 | A1 | 6/2006 | Ohno et al. | |
| 2006/0194970 | A1 | 8/2006 | Kakiya | |

FOREIGN PATENT DOCUMENTS

| EP | 464846 A1 * | 1/1992 |
| EP | 1726952 A1 | 11/2006 |
| JP | 2003-176228 * | 6/2003 |
| JP | 2003-176228 A | 6/2003 |
| WO | WO02/24166 * | 3/2002 |
| WO | WO-02/24166 A | 3/2002 |
| WO | WO-2004/113333 A | 12/2004 |
| WO | WO-2005/009999 A | 2/2005 |
| WO | WO-2005/009999 A | 2/2005 |
| WO | WO-2006/096439 A2 | 9/2006 |

OTHER PUBLICATIONS

Lopatin et al "The use of non-aqueous solvents to prepare injection solutions", vol. 6, No. 11, 724-733, 1972.*
Remington's 17th Edition Pharmaceutical sciences, 1985, chapter 76.*
Eichbaum et al "Antiarrhythmic effect of solvents: propylene glycol, benzyl alcohol" Basic Research in Cardiology, vol. 71, No. 4, 1976, pp. 355-370.*
Witchel et al "Psychotropic drugs, cardiac arrhymia, and sudden death" Review Article, J. Clin. Psychopharmacol 2003;23: 58-77.*
Oct. 29, 2010 Extended European search report for Int'l Appl No. PCT/JP2006311739.
Office Action issued in Japanese Application No. 2007-521271 on Jul. 5, 2011.
Dictionary of Medicinal Additives, Yakuji Nippo Limited, 1st Ed., pp. 95-96, 114-116, 132, 185 (1994).

* cited by examiner

*Primary Examiner* — Brandon Fetterolf
*Assistant Examiner* — Jean Cornet
(74) *Attorney, Agent, or Firm* — Birch, Stewart, Kolasch & Birch, LLP

(57) ABSTRACT

A solution-type preparation of lurasidone comprising N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptanedicarboxyimide hydrochloride (lurasidone) as an active ingredient and containing at least one substance selected from benzyl alcohol, N,N-dimethylacetamide, lactic acid and propylene glycol.

9 Claims, No Drawings

SOLUBILIZATION PREPARATION

This application is the national stage of the International Application No. PCT/JP2006/311739 filed in Japan on Jun. 12, 2006, which in turn claims priority under 35 USC 119(a)-(d) of Japanese Application No. JP 2005-172725, filed in the Japanese Patent Office on Jun. 13, 2005.

TECHNICAL FIELD

The present invention relates to a solution-type preparation comprising as an active ingredient a free form of N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptanedicarboxyimide hydrochloride (lurasidone) or a pharmaceutically acceptable acid addition salt thereof. More particularly, the present invention relates to a solution-type preparation wherein a free form of lurasidone or a pharmaceutically acceptable acid addition salt thereof is solubilized.

BACKGROUND ART

A free form of lurasidone and an acid addition salt thereof are known to have psychotropic activities and are effective as therapeutic agents, particularly for schizophrenia or senile dementia, etc. Senile dementia is broadly classified into Alzheimer's dementia and cerebrovascular dementia, and it can be said that the two make up about 80% of senile dementia. In accordance with rapid aging of the population, the number of patients with dementia tends to increase and among the population of 65 or more years old about 7% is estimated to be suffered from dementia in Japan, and hence, developments of effective therapeutic agents for dementia are desired. Lurasidone is known to be administered orally or parenterally, and methods for administering in the form of a solid preparation, such as tablet or capsule, or as a liquid preparation for an oral preparation and as an injection or suppository for a parenteral preparation are disclosed in Patent Document 1. Administration of an oral preparation, particularly a solid preparation, is usually believed to be the most common and preferable in treatment for many diseases. However, patients with schizophrenia or senile dementia individually have wide-ranging symptoms, and hence, it is sometimes not sufficient to treat such patients only with oral solid preparations, for example in case of administration to patients with schizophrenia in acute stage, patients of drug refusal or aged patients.

If a free form of hardly-soluble lurasidone or an acid addition salt thereof can be prepared in the form of a solution-type preparation, it may be usable in wider-ranging preparations including parenteral preparations (e.g. injections), or oral liquid preparations, and it may provide various, convenient and effective methods for treatment of much more patients. However, since lurasidone or a free form thereof has a solubility of less than several µg/mL in water, it has hitherto been very difficult to prepare an aqueous solution-type preparation containing a high concentration of lurasidone or a free form thereof. Additionally, no method for solubilizing lurasidone and a free form thereof has been known so far. In case of using a solution-type preparation for parenteral administration such as an injection, there are potential problems such as local irritation, hemolysis, neurotoxicity, etc. depending on the kinds of organic solvents, and hence, the dose of the organic solvent or contents in a solution are limited, and accordingly, it is required to reduce the amount of the organic solvent.

Patent Document 1: JP2800953

DISCLOSURE OF INVENTION

Problems to be Resolved by the Invention

An object of the present invention is to provide a solution-type preparation wherein a free form of lurasidone and an acid addition salt thereof are solubilized, which is for treatment of a patient with schizophrenia or senile dementia.

Means of Solving the Problems

According to the intensive study, the present inventors have found that a hardly-soluble lurasidone, having a solubility in water of less than several µg/mL, can be solubilized at about 10,000 to 200,000 times higher concentrations by incorporating at least one substance selected from benzyl alcohol, N,N-dimethylacetamide, lactic acid and propylene glycol, and a solution-type preparation with high stability can be prepared. The objects can be achieved according to the following means.

The present invention includes the following embodiments:

(1) A solution-type preparation comprising as an active ingredient N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptane-dicarboxyimide, which is a free form of lurasidone, or a pharmaceutically acceptable acid addition salt thereof, wherein the active ingredient is solubilized by incorporating at least one substance selected from benzyl alcohol, N,N-dimethylacetamide, lactic acid, anhydrous ethanol and propylene glycol.

(2) The solution-type preparation of (1), which is in the form of a parenteral preparation.

(3) The solution-type preparation of either of (1) or (2), which is for intravenous, intramuscular, subcutaneous or intracutaneous injection.

(4) The solution-type preparation of (1), which is in the form of an oral liquid preparation.

(5) The solution-type preparation of any one of (1) to (4) for the treatment of schizophrenia or senile dementia, which comprises lurasidone or a pharmaceutically acceptable acid addition salt thereof in an amount of therapeutically effective for treating said mental disease.

(6) The solution-type preparation of any one of (1) to (5) comprising the active ingredient in a concentration of 1 to 100 mg/mL.

(7) The solution-type preparation of either of (2) or (3) comprising the active ingredient in a concentration of 1 to 20 mg/mL.

(8) The solution-type preparation of any one of (1) to (5) comprising lurasidone and 5 to 25% (W/W) of anhydrous ethanol.

(9) The solution-type preparation of any one of (1) to (5) comprising lurasidone and 2 to 15% (W/W) of benzyl alcohol.

Effects of the Invention

Solubilization of lurasidone and an acid addition salt thereof at high concentrations allows to formulate wide-ranging preparations such as injections, external preparations or oral liquid preparations, and to provide various, convenient and effective methods for treatment of much more patients.

BEST MODE FOR CARRYING OUT THE INVENTION

N-[4-[4-(1,2-benzisothiazol-3-yl)-1-piperazinyl]-(2R,3R)-2,3-tetramethylene-butyl]-(1'R,2'S,3'R,4'S)-2,3-bicyclo

[2,2,1]heptane-dicarboxyimide, which is a free form of lurasidone, and an acid addition salt thereof are effective as a psychotropic agent, particularly as a therapeutic agent for schizophrenia, and can be administered in the form of a preparation for oral or parenteral administration (see JP2800953).

An acid addition salt of a free form of lurasidone includes an addition salt with a pharmaceutically acceptable inorganic acid or organic acid. The inorganic acid includes, for example, hydrochloric acid, hydrobromic acid, hydroiodic acid, hydrofluoric acid, etc., and the organic acid includes, for example, phosphoric acid, acetic acid, oxalic acid, citric acid, malic acid, tartaric acid, maleic acid, fumaric acid, etc. A preferable salt is hydrochloride.

Dosage for oral administration is 5 to 200 mg, preferably 40 to 120 mg, per day. It may be administered by dividing for several times a day, but preferably at one time a day. For parenteral administration, particularly injection by intravenous, intramuscular, subcutaneous or intracutaneous route, the dose is in the range of 0.1 to 40 mg, preferably 0.2 to 20 mg, more preferably 0.4 to 10 mg, per day. It may be administered by dividing for several times a day, but preferably at one time a day.

The solution-type preparation of the present invention refers to an aqueous or oily pharmaceutical composition wherein an active ingredient and an additive exist in solubilized states, preferably an aqueous preparation. The preferable additive includes benzyl alcohol, N,N-dimethylacetamide, lactic acid, anhydrous ethanol or propylene glycol. The aqueous preparation can be prepared by mixing a free form of lurasidone or an acid addition salt thereof and an additive with water. The oily preparation can be prepared by mixing a free form of lurasidone or an acid addition salt thereof with an additive, and if necessary with a pharmaceutically acceptable oil. Other additives except the above additives may be optionally added. The pharmaceutically acceptable oil includes sesame oil, castor oil, arachis oil, camellia oil, soybean oil, olive oil, mint oil, etc.

The solution-type preparation of the present invention may be used as a parenteral preparation such as injection or external preparation as well as a liquid preparation for oral administration.

The solution-type preparation of the present invention comprises lurasidone as an active ingredient in a concentration of 0.2 to 160 mg/mL, preferably 1 to 100 mg/mL. More specifically, a parenteral preparation such as injection comprises the active ingredient in a concentration of preferably 0.2 to 40 mg/mL, more preferably 0.5 to 30 mg/mL, further preferably 1 to 20 mg/mL, and a liquid preparation for oral administration comprises it in a concentration of preferably 2 to 160 mg/mL, more preferably 4 to 100 mg/mL, further preferably 10 mg/mL to 80 mg/mL.

The solution-type preparation of the present invention may contain anhydrous ethanol in an amount of 2.5 to 40% (W/W), preferably 5 to 25% (W/W) on the basis of weight of the preparation.

The solution-type preparation of the present invention may contain benzyl alcohol in an amount of 1 to 25% (W/W), preferably 2 to 15% (W/W) on the basis of weight of the preparation.

The solution-type preparation of the present invention is required to be designed a preparation with a potential of long life and high stability, and specifically, preferable one includes a formulation wherein total UK peak is 1.5% or less, particularly 1.0% or less, at 60° C. for 4 weeks.

The solution-type preparation of the present invention may be optionally used with other adjuvant such as solubilization agent, buffering agent, preservative, antioxidant, stabilizing agent, tonicity agent, sweetening agent, sweetener, flavoring agent, organic acid, inorganic acid, amino acid, etc.

The additive is not specified but includes one which is conventionally used in pharmaceuticals. The buffering agent may include, for example, acetic acid, phosphoric acid, boric acid or a salt thereof, etc. The preservative includes, for example, benzoic acid, sodium benzoate, sodium sulfite, salicylic acid, sodium salicylate, dibutylhydroxytoluene, sorbic acid, potassium sorbate, sodium dehydroacetate, isobutyl paraoxybenzoate, isopropyl paraoxybenzoate, ethyl paraoxybenzoate, methyl paraoxybenzoate, etc. The antioxidant includes, for example, sodium nitrite, ascorbic acid, sodium hydrogen sulfite, sodium edetate, erythorbic acid, cysteine hydrochloride, tocopherol, soy lecithin, sodium thioglycolate, sodium thiomalate, tocopherol, sodium pyrosulfite, butylhydroxyanisole, propyl gallate, etc. The tonicity agent includes, for example, sodium chloride, mannitol, sorbitol, xylitol, fructose, lactose, glucose, sodium sulfate, citric acid, sodium citrate, glycerin, boric acid, phosphoric acid, sodium hydrogen phosphate, sodium dihydrogen phosphate, sodium hydroxide, sodium hydrogen carbonate, calcium bromide, sodium bromide, etc. The organic acid includes, for example, acetic acid, etc. The inorganic acid includes, for example, phosphoric acid, sulfuric acid, etc. The amino acid includes, for example, lactic acid, tartaric acid, glycine, etc.

The present invention is more specifically illustrated by the following Examples and comparative experiments, but is not necessarily limited thereto.

EXAMPLES

Example 1

Solubilities of lurasidone or a free form thereof were studied by using additives listed in Table 1 (unit: mg/mL). Solid-type additives were studied in 10% aqueous solutions thereof and liquid-type ones were studied in 100% solutions thereof. Specifically, to 10% aqueous solution of solid-type additive or to 100% solution of liquid-type one was added lurasidone or a free form thereof so that a concentration thereof was 10 mg/mL, and the mixture was promoted to be dissolved by an operation such as stirring, heating or sonication. It was confirmed by visual check 30 minutes after the operation whether the mixture was perfectly dissolved. In case that the mixture was perfectly dissolved in a concentration of 10 mg/mL, another amount of lurasidone or a free form thereof was added to be evaluated.

As a result of the study, a solubility of lurasidone or a free form thereof was remarkably improved only in case of using benzyl alcohol, N,N-dimethylacetamide, lactic acid or propylene glycol.

TABLE 1

| No. | Additive | A free form of lurasidone | Lurasidone |
|---|---|---|---|
| 1 | Citric acid | — | <10 |
| 2 | Sodium citrate | — | <10 |
| 3 | L-Aspartic acid | — | <10 |
| 4 | L-Arginine | — | <10 |
| 5 | Soy lecithin | — | <10 |
| 6 | Polysorbate 80 | — | <10 |
| 7 | D-Mannitol | — | <10 |
| 8 | Sodium hydrogen carbonate | — | <10 |
| 9 | β-Cyclodextrin | — | <10 |
| 10 | Maleic acid | — | <10 |
| 11 | Ethyl oleate | — | <10 |

TABLE 1-continued

| No. | Additive | A free form of lurasidone | Lurasidone |
|---|---|---|---|
| 12 | Calcium bromide | — | <10 |
| 13 | Ethylene diamine hydrochloride | — | <10 |
| 14 | Tris | — | <10 |
| 15 | Polyethylene glycol 400 | — | <10 |
| 16 | Nicotinic amide | — | <10 |
| 17 | Capric acid | — | <10 |
| 18 | Concentrated glycerin | — | <10 |
| 19 | Propylene glycol | — | 30 to 100 |
| 20 | Lactic acid | — | >100 |
| 21 | Squalane | <10 | <10 |
| 22 | Medium-chain triglyceride | <10 | <10 |
| 23 | Benzyl benzoate | <10 | — |
| 24 | Anhydrous ethanol | <10 | — |
| 25 | Sorbitan sesquioleate | <10 | — |
| 26 | 1,3-Butanediol | <10 | — |
| 27 | Dipropylene glycol | <10 | — |
| 28 | Triethyleneglycol | <10 | — |
| 29 | Isopropyl alcohol | <10 | — |
| 30 | Benzyl alcohol | 100 to 200 | >200 |
| 31 | Isostearic acid | 10 to 30 | — |
| 32 | Isopropyl myristate | <10 | — |
| 33 | Diethyl sebacate | 10 to 30 | — |
| 34 | Monoethanolamine | <10 | — |
| 35 | Diethanolamine | <10 | — |
| 36 | Triethanolamine | <10 | — |
| 37 | Liquid paraffin | <10 | — |
| 38 | Toluene | >50 | — |
| 39 | Ethyl acetate | 10 to 30 | — |
| 40 | Crotamiton | 10 to 30 | — |
| 41 | N-Methyl-2-pyrrolidone | >50 | — |
| 42 | Glycol salicylate | <10 | — |
| 43 | Oleic acid | 30 to 50 | — |
| 44 | Triacetin | <10 | — |
| 45 | N,N-Dimethylacetamide | 80 to 100 | — |
| 46 | Sesame oil | <10 | 1 to 10 |
| 47 | Castor oil | <10 | 1 to 10 |
| 49 | Arachis oil | <10 | 1 to 10 |
| 50 | Camellia oil | <10 | 1 to 10 |
| 51 | Soybean oil | <10 | 1 to 10 |
| 52 | Olive oil | <10 | <1 |
| 53 | Mint oil | 10 to 30 | — |

Example 2

Solutions comprising lurasidone and a hydrochloride thereof in a concentration of 30 mg/mL were prepared in formulations in Table 2 to be stored under warming conditions (60° C. and 40° C.). After one-month storage, a residual ratio of principal agent was measured by using reverse phase HPLC. As a result of the study, lurasidone and a free form thereof were confirmed to be stable in aqueous solutions using benzyl alcohol, propylene glycol, N,N-dimethylacetamide and lactic acid which were found to show excellent effects as solubilization agents in Example 1. In other words, the present invention can provide a solution-type preparation with high stability wherein lurasidone and a free form thereof are solubilized at high concentrations.

HPLC conditions:
Column: YMC-Pack AM-312 (5 μm, 6.0 mmφ×150 mm, manufactured by YMC Co., Ltd.)
Detector: ultraviolet absorptiometer (measured wavelength: 230 nm)
Column temperature: constant temperature around 25° C.
Mobile Phase:
Solution A: 0.025% aqueous trifluoroacetic acid solution/acetonitrile mixture (4:1)
Solution B: 0.025% trifluoroacetic acid in acetonitrile solution
Flow rate: 1.0 mL/min
Gradient conditions:

| Time (min) | 0.0 | 60 | 60.1 | 75.0 |
|---|---|---|---|---|
| Mobile phase Solution B (%) | 10.0 | 60.0 | 10.0 | 10.0 |

TABLE 2

| Formulation | Active ingredient | Solvent | Residual ratio (vs Initial) 60° C. × 1M | 40° C. × 1M |
|---|---|---|---|---|
| Formulation 1 | Lurasidone | BA:PG:Water = 1:1:1 | 97.7% | 99.8% |
| Formulation 2 | A free form of lurasidone | DMA:LA:Water = 1:1:1 | 99.5% | 99.7% |

BA: benzyl alcohol
PG: propylene glycol
DMA: N,N-dimethylacetamide
LA: lactic acid
Water: purified water (MILLI-Q water (MILLI-Q SP REAGENT WATER SYSTEM manufactured by MILLIPORE))

Example 3

Propylene Glycol Formulation

Solubilities of lurasidone were studied by using additives listed in Table 3. Each mixture was promoted to be dissolved by an operation such as stirring, heating (at about 70° C.) or sonication, and it was confirmed by visual check 30 minutes after the operation whether each mixture was perfectly dissolved. Solubilities were evaluated as O in case that a mixture was perfectly dissolved and as X in case that a mixture was not perfectly dissolved or was precipitated during cooling to room temperature.

As a result of the study, formulations which were dissolved in case of using propylene glycol and water for injection on conditions that anhydrous ethanol therein was in the range of 5 to 33% (w/w) could be found.

TABLE 3

| Sample No. | Lurasidone (mg/mL) | Anhydrous ethanol (%) | Propylene glycol (%) | Water for injection (%) | Solubility evaluation |
|---|---|---|---|---|---|
| IM162 | 10 | 2.5 | 75 | 21.5 | X |
| IM163 | 10 | 2.5 | 96.5 | 0 | O |
| IM164 | 10 | 5 | 60 | 34 | X |
| IM165 | 10 | 5 | 75 | 19 | O |
| IM166 | 10 | 5 | 94 | 0 | O |
| IM167 | 10 | 10 | 60 | 29 | X |
| IM168 | 10 | 10 | 75 | 14 | O |
| IM169 | 10 | 10 | 89 | 0 | O |
| IM079 | 10 | 15 | 50 | 34 | X |
| IM080 | 10 | 15 | 60 | 24 | O |
| IM081 | 10 | 15 | 75 | 9 | O |

TABLE 3-continued

| Sample No. | Lurasidone (mg/mL) | Anhydrous ethanol (%) | Propylene glycol (%) | Water for injection (%) | Solubility evaluation |
|---|---|---|---|---|---|
| IM082 | 10 | 15 | 84 | 0 | ○ |
| IM086 | 10 | 25 | 33 | 41 | X |
| IM087 | 10 | 25 | 50 | 24 | ○ |
| IM088 | 10 | 25 | 60 | 14 | ○ |
| IM089 | 10 | 25 | 74 | 0 | ○ |
| IM093 | 10 | 33 | 33 | 33 | X |
| IM094 | 10 | 33 | 50 | 16 | ○ |
| IM095 | 10 | 33 | 60 | 6 | ○ |
| IM096 | 10 | 33 | 66 | 0 | ○ |

Water for injection: water for injection in Japanese Pharmacopoeia, Otsuka distilled water (manufactured by Otsuka Pharmaceutical Co., Ltd.)

Example 4

Benzyl Alcohol-Added Formulation

Solubilities of lurasidone were studied by using additives listed in Table 4. Each mixture was promoted to be dissolved by an operation such as stirring, heating (at about 70° C.) or sonication, and it was confirmed by visual check 30 minutes after the operation whether each mixture was perfectly dissolved. Solubilities were evaluated as O in case that a mixture was perfectly dissolved and as X in case that a mixture was not perfectly dissolved or was precipitated during cooling to room temperature.

As a result of the study, formulations which were dissolved in case of using propylene glycol and water for injection on conditions that benzyl alcohol therein was in the range of 1 to 25% (w/w) could be found.

TABLE 4

| Sample No. | Lurasidone (mg/mL) | Benzyl alcohol (%) | Propylene glycol (%) | Water for injection (%) | Solubility evaluation |
|---|---|---|---|---|---|
| IM171 | 10 | 1 | 75 | 23 | X |
| IM172 | 10 | 1 | 98 | 0 | ○ |
| IM173 | 10 | 2 | 60 | 37 | X |
| IM174 | 10 | 2 | 75 | 22 | ○ |
| IM175 | 10 | 2 | 97 | 0 | ○ |
| IM176 | 10 | 3 | 60 | 36 | X |
| IM177 | 10 | 3 | 75 | 21 | ○ |
| IM178 | 10 | 3 | 96 | 0 | ○ |
| IM179 | 10 | 4 | 60 | 35 | X |
| IM180 | 10 | 4 | 75 | 20 | ○ |
| IM181 | 10 | 4 | 95 | 0 | ○ |

TABLE 4-continued

| Sample No. | Lurasidone (mg/mL) | Benzyl alcohol (%) | Propylene glycol (%) | Water for injection (%) | Solubility evaluation |
|---|---|---|---|---|---|
| IM143 | 10 | 5 | 60 | 34 | X |
| IM144 | 10 | 5 | 75 | 19 | ○ |
| IM145 | 10 | 5 | 94 | 0 | ○ |
| IM108 | 10 | 15 | 25 | 59 | X |
| IM109 | 10 | 15 | 33 | 51 | ○ |
| IM110 | 10 | 15 | 50 | 34 | ○ |
| IM111 | 10 | 15 | 60 | 24 | ○ |
| IM112 | 10 | 15 | 75 | 9 | ○ |
| IM113 | 10 | 15 | 84 | 0 | ○ |
| IM116 | 10 | 25 | 25 | 49 | X |
| IM117 | 10 | 25 | 33 | 41 | ○ |
| IM118 | 10 | 25 | 50 | 24 | ○ |
| IM119 | 10 | 25 | 60 | 14 | ○ |
| IM120 | 10 | 25 | 74 | 0 | ○ |

Example 5

Stability Test of Anhydrous Ethanol-Added Formulation

Stability tests were carried out for some formulations (anhydrous ethanol: 15, 25, 33%) which could be solubilized in the previous study of anhydrous ethanol-added formulations.
HPLC conditions:
Column: YMC-Pack Pro C18 (5 μm, 6.0 mmφ×150 mm, manufactured by YMC Co., Ltd.)
Detector: ultraviolet absorptiometer (measured wavelength: 230 nm)
Column temperature: constant temperature around 25° C.
Mobile Phase:
  Solution A: 5 mmol/L phosphate buffer (pH 7.0)/acetonitrile mixture (4:1)
  Solution B: acetonitrile
Flow rate: 1.1 mL/min
Gradient conditions:

| Time (min) | 0.0 | 5.0 | 35.0 | 65.0 | 65.1 | 80.0 |
|---|---|---|---|---|---|---|
| Mobile phase Solution B (%) | 50.0 | 50.0 | 87.0 | 87.0 | 50.0 | 50.0 |

As a result of analysis, samples IM080 to IM094 in Table 5 were stable, wherein total UK peaks were 1.5% or less. Particularly, samples IM080 and IM087 were confirmed very high stabilities, wherein total UK peaks were 1.0% or less.

TABLE 5

| Sample No. | Lurasidone (mg/mL) | Anhydrous ethanol (%) | Propylene glycol (%) | Water for injection (%) | 60° C. × 4 W Contents (%) | Total UK peak (%) |
|---|---|---|---|---|---|---|
| IM080 | 10 | 15 | 60 | 24 | 99.6 | 0.42 |
| IM081 | 10 | 15 | 75 | 9 | 98.9 | 1.09 |
| IM082 | 10 | 15 | 84 | 0 | 99.0 | 1.02 |
| IM087 | 10 | 25 | 50 | 24 | 99.4 | 0.58 |
| IM088 | 10 | 25 | 60 | 14 | 98.9 | 1.08 |
| IM089 | 10 | 25 | 74 | 0 | 98.7 | 1.34 |
| IM094 | 10 | 33 | 50 | 16 | 98.9 | 1.11 |
| IM095 | 10 | 33 | 60 | 6 | 98.1 | 1.89 |
| IM096 | 10 | 33 | 66 | 0 | 98.3 | 1.69 |

Example 6

Stability Test of Benzyl Alcohol-Added Formulation

Stability tests were carried out for some formulations (benzyl alcohol: 5, 15, 25%) which were solubilized in the previous study of benzyl alcohol-added formulations.
HPLC conditions:
Column: YMC-Pack Pro C18 (5 µm, 6.0 mmφ×150 mm, manufactured by YMC Co., Ltd.)
Detector: ultraviolet absorptiometer (measured wavelength: 230 nm)
Column temperature: constant temperature around 25° C.
Mobile Phase:
 Solution A: 5 mmol/L phosphate buffer (pH7.0)/acetonitrile mixture (4:1)
 Solution B: acetonitrile
Flow rate: 1.1 mL/min
Gradient conditions:

| Time (min) | 0.0 | 5.0 | 35.0 | 65.0 | 65.1 | 80.0 |
|---|---|---|---|---|---|---|
| Mobile phase Solution B (%) | 50.0 | 50.0 | 87.0 | 87.0 | 50.0 | 50.0 |

As a result of analysis, samples IM144, IM145, IM109 to IM111, IM117 and IM118 in Table 6 were stable, wherein total UK peaks were 1.5% or less. Particularly, samples IM144, IM109, IM110, IM111 and IM117 were confirmed very high stabilities, wherein total UK peaks were 1.0% or less.

formulations. Additionally, benzyl alcohol amounts (W/W) were allowed to be reduced by addition of acetic acid.
HPLC conditions:

Column: YMC-Pack Pro C18 (5 µm, 6.0 mmφ×150 mm, manufactured by YMC Co., Ltd.)

Detector: ultraviolet absorptiometer (measured wavelength: 230 nm)

Column temperature: constant temperature around 25° C.

Mobile Phase:
 Solution A: 5 mmol/L phosphate buffer (pH 7.0)/acetonitrile mixture (4:1)
 Solution B: acetonitrile
Flow rate: 1.1 mL/min
Gradient conditions:

| Time (min) | 0.0 | 5.0 | 35.0 | 65.0 | 65.1 | 80.0 |
|---|---|---|---|---|---|---|
| Mobile phase Solution B (%) | 50.0 | 50.0 | 87.0 | 87.0 | 50.0 | 50.0 |

TABLE 6

| Sample No. | Lurasidone (mg/mL) | Benzyl alcohol (%) | Propylene glycol (%) | Water for jinection (%) | 60° C. × 4 W Contents (%) | 60° C. × 4 W Total UK peak (%) |
|---|---|---|---|---|---|---|
| IM144 | 10 | 5 | 75 | 19 | 99.5 | 0.49 |
| IM145 | 10 | 5 | 94 | 0 | 98.8 | 1.24 |
| IM109 | 10 | 15 | 33 | 51 | 99.4 | 0.57 |
| IM110 | 10 | 15 | 50 | 34 | 99.5 | 0.53 |
| IM111 | 10 | 15 | 60 | 24 | 99.3 | 0.74 |
| IM112 | 10 | 15 | 75 | 9 | 97.8 | 2.20 |
| IM113 | 10 | 15 | 84 | 0 | 74.2 | 25.8 |
| IM117 | 10 | 25 | 33 | 41 | 99.3 | 0.73 |
| IM118 | 10 | 25 | 50 | 24 | 98.6 | 1.44 |
| IM119 | 10 | 25 | 60 | 14 | 96.9 | 3.07 |
| IM120 | 10 | 25 | 74 | 0 | 62.6 | 37.4 |

Example 7

Benzyl Alcohol- and Acetic Acid-Added Formulation

Stability tests were carried out for the following dissolved formulations among benzyl alcohol- and acetic acid-added

TABLE 7

| | | Component ratio of additives (%) | | | | | |
|---|---|---|---|---|---|---|---|
| Sample No. | Lurasidone (mg/mL) | Benzyl alcohol | Propylene glycol | Acetic acid | Water for injection | Initial | 60° C. × 1M |
| IM041 | 10 | 33 | 33 | | 34 | 99.7 | 90.4 |
| IM051 | | 10 | 30 | 1 | 59 | 99.7 | 94.2 |
| IM055 | | 10 | 30 | 2 | 58 | 99.5 | 86.5 |

Example 8

N,N-dimethylacetamide- and Acid-Added Formulation

Stability tests were carried out for the following dissolved formulations among N,N-dimethylacetamide- and acid-added formulations, and it was confirmed that any formulations showed high stabilities.

HPLC conditions:
Column: YMC-Pack Pro C18 (5 μm, 6.0 mmφ×150 mm, manufactured by YMC Co., Ltd.)
Detector: ultraviolet absorptiometer (measured wavelength: 230 nm)
Column temperature: constant temperature around 25° C.
Mobile Phase:
  Solution A: 5 mmol/L phosphate buffer (pH 7.0)/acetonitrile mixture (4:1)
  Solution B: acetonitrile
Flow rate: 1.1 mL/min
Gradient conditions:

| Time (min) | 0.0 | 5.0 | 35.0 | 65.0 | 65.1 | 80.0 |
|---|---|---|---|---|---|---|
| Mobile phase Solution B (%) | 50.0 | 50.0 | 87.0 | 87.0 | 50.0 | 50.0 |

TABLE 8

| | | Component ratio of additive | | | | |
|---|---|---|---|---|---|---|
| Sample No. | Lurasidone (mg/mL) | N,N-Dimethylacetamide | Acid | Water for injection | Initial | 60° C. × 1M |
| IM045 | 10 | 33 | 33 (lactic acid) | 34 | 99.3 | 99.4 |
| IM047 | | | 33 (acetic acid) | | 99.3 | 99.8 |
| IM049 | | | 33 (phosphoric acid) | | 99.6 | 99.4 |
| IM046 | 30 | 33 | 33 (lactic acid) | 34 | 100.0 | 99.9 (99.5) |
| IM048 | | | 33 (acetic acid) | | 100.0 | 99.8 |

INDUSTRIAL APPLICABILITY

The present invention provides wider-ranging preparations including parenteral preparations such as injections and external preparations and oral liquid preparations by solubilizing lurasidone and a free form thereof in a high concentration, and thereby provides effective treatment of much more patients with various symptoms.

The invention claimed is:

1. A stable aqueous solution-type preparation comprising as an active ingredient N-[4-[4-(1,2-benzisothiazol-3-yl)-1-piperazinyl]-(2R,3R)-2,3-tetramethylene-butyl]-(1'R,2'S,3'R,4'S)-2,3-bicyclo[2,2,1]heptanedicarboxylmide, which is a free form of lurasidone, or a pharmaceutically acceptable acid addition salt thereof, wherein the active ingredient is solubilized by the following additives (i)
  (i) 50 to 75% (W/W) of propylene glycol, 6 to 24% (W/W) of water and 5 to 33% (W/W) of anhydrous ethanol, and the active ingredient is present in a concentration of 1 to 20 mg/mL.

2. The stable aqueous solution-type preparation of claim 1, which is for intravenous, intramuscular, subcutaneous or intracutaneous injection.

3. The stable aqueous solution-type preparation of claim 1 for the treatment of schizophrenia or senile dementia, which comprises a free form of lurasidone or a pharmaceutically acceptable acid addition salt thereof in an amount therapeutically effective for treating said mental disease.

4. The stable aqueous solution-type preparation of claim 1, wherein the active ingredient is solubilized by the additives (i) in the amounts 50 to 75% (W/W) of propylene glycol, 9 to 24% (W/W) of water and 15 to 33% (W/W) of anhydrous ethanol.

5. A stable aqueous solution-type preparation that is one selected from the group consisting of preparations i) to viii) set forth below:

| Preparation | Lurasidone (mg/mL) | Anhydrous ethanol (%) | Propylene glycol (%) | Water for injection (%) |
|---|---|---|---|---|
| i) | 10 | 5 | 75 | 19 |
| ii) | 10 | 10 | 75 | 14 |
| iii) | 10 | 15 | 60 | 24 |

-continued

| Preparation | Lurasidone (mg/mL) | Anhydrous ethanol (%) | Propylene glycol (%) | Water for injection (%) |
|---|---|---|---|---|
| iv) | 10 | 15 | 75 | 9 |
| v) | 10 | 25 | 50 | 24 |
| vi) | 10 | 25 | 60 | 14 |
| vii) | 10 | 33 | 50 | 16 |
| viii) | 10 | 33 | 60 | 6. |

6. The stable aqueous solution-type preparation of claim 1, which is in the form of a parenteral preparation.

7. The stable aqueous solution-type preparation of claim 1, which is in the form of an oral liquid preparation.

8. The stable aqueous solution-type preparation of claim 1, wherein said preparation is a formulation exhibiting a total UK peak of 1.5% or less after storage at 60° C. for 4 weeks.

9. The stable aqueous solution-type preparation of claim 8, wherein the total UK peak is 1.0% or less.

* * * * *